(12) United States Patent
Kwon et al.

(10) Patent No.: US 8,614,285 B2
(45) Date of Patent: Dec. 24, 2013

(54) PHOTOSENSITIZER BASED ON POLYMER DERIVATIVES-PHOTOSENSITIZER CONJUGATES FOR PHOTODYNAMIC THERAPY

(75) Inventors: Ick-Chan Kwon, Seoul (KR); Kui-Won Choi, Seoul (KR); Kwang-Meyung Kim, Seoul (KR); In-Chan Youn, Seoul (KR); Jong-Ho Kim, Seoul (KR); Kyeong-Soon Park, Jeollanam-Do (KR)

(73) Assignee: Korea Institute of Science and Technology (KR)

( * ) Notice: Subject to any disclaimer, the term of this patent is extended or adjusted under 35 U.S.C. 154(b) by 313 days.

(21) Appl. No.: 12/595,103

(22) PCT Filed: Apr. 23, 2008

(86) PCT No.: PCT/KR2008/002283
§ 371 (c)(1),
(2), (4) Date: Oct. 8, 2009

(87) PCT Pub. No.: WO2008/130181
PCT Pub. Date: Oct. 30, 2008

(65) Prior Publication Data
US 2010/0222538 A1    Sep. 2, 2010

(30) Foreign Application Priority Data

Apr. 23, 2007  (KR) .................. 10-2007-0039522
Apr. 18, 2008  (KR) .................. 10-2008-0036214

(51) Int. Cl.
*C08F 251/00*    (2006.01)
*A61K 31/555*    (2006.01)

(52) U.S. Cl.
USPC ......... 527/312; 424/422; 424/450; 424/136.1

(58) Field of Classification Search
USPC ................ 527/312; 514/6, 176, 54, 185, 410; 530/391.1, 400, 17.4
See application file for complete search history.

(56) References Cited

U.S. PATENT DOCUMENTS

| | | |
|---|---|---|
| 5,053,423 A | 10/1991 | Liu |
| 2003/0153547 A1 * | 8/2003 | Aida et al. .................... 514/185 |
| 2007/0059316 A1 * | 3/2007 | Pallenberg et al. ........ 424/178.1 |

OTHER PUBLICATIONS

Korean Office Action mailed May 28, 2010 in connection with corresponding Korean Application No. 10-2008-0036214.
International Search Report and Written Opinion dated Sep. 4, 2008 issued in corresponding PCT Application No. PCT/KR2008/002283.
Tegos et al 'Protease-Stable Polycationic Photosensitizer Conjugates between Polyethyleneimine & Chlorin(e6) for Broad Spectrum Antimicrobial Photoinactivation' Antimicrob Agents Chemother, pp. 1402-10 vol. 50(4), Apr. 2006.
Michael R. Hamblin et al 'Pegylation of a Chlorine6 Polymer Conjugate Increases Tumor Targeting of Photosensitizer' Cancer Res., pp. 7155-7162 vol. 61, Oct. 2001.

* cited by examiner

*Primary Examiner* — James J Seidleck
*Assistant Examiner* — S. Camilla Pourbohloul
(74) *Attorney, Agent, or Firm* — Ostrolenk Faber LLP

(57) ABSTRACT

Disclosed is a novel photosensitizer based on polymer derivatives-photosensitizer conjugates for photodynamic therapy capable of being selectively accumulated in cancerous tissues and producing singlet oxygen or free radical by laser irradiation. The polymer derivatives-photosensitizer conjugates for photodynamic therapy are prepared as nano-sized particles, and have excellent selection and accumulation ratio for cancerous tissues. The photosensitizer conjugates can produce singlet oxygen or free radical by a specific laser wavelength. Owing to the excellent selection and accumulation ratio for cancerous tissues, the conjugates minimizes photo-cytotoxicity of the conventional photosensitizer having a low molecular amount. Accordingly, the conjugates are very useful as a photosensitizes for photodynamic therapy with reduced side effects and excellent therapeutic effectiveness.

3 Claims, 9 Drawing Sheets

PHOTOSENSITIZER BASED ON POLYMER DERIVATIVES-PHOTOSENSITIZER CONJUGATES FOR PHOTODYNAMIC THERAPY

CROSS-REFERENCE TO RELATED APPLICATIONS

The present application is a 35 U.S.C. §§371 national phase conversion of PCT/KR2008/002283, filed Apr. 23, 2008, which claims priority of Korean Patent Application Nos. 10-2007-0039522 and 10-2008-0036214, filed Apr. 23, 2007 and Apr. 18, 2008, respectively. The PCT International Application was published in the English language.

TECHNICAL FIELD

The present invention relates to a novel photosensitizer based on biocompatible polymer derivatives-photosensitizer conjugates for photodynamic therapy, and more particularly, to a novel photosensitizer based on polymer derivatives-photosensitizer conjugates for photodynamic therapy capable of remarkably increasing selection degree and accumulation ratio for cancerous tissues and remarkably reducing photo-cytotoxicity by chemically reforming the conventional photosensitizer into polymer derivatives having a cancer targeting characteristic.

BACKGROUND ART

Generally, a photodynamic therapy is one of the most spotlighted therapies for cancer. According to the photodynamic therapy, once a photosensitizer sensitive to light is put into a human body under light irradiated from outside, abundant oxygen in the human's body and the external light chemically react with each other, thereby producing singlet oxygen or free radical. The singlet oxygen or free radical serve to destroy each kind of disease tissues or cancer cells.

The photodynamic therapy has advantages that only cancer cells can be removed with maintaining normal cells, and local anesthesia can be simply performed with excluding danger from general anesthesia. The photodynamic therapy has been intensively researched since 1980's, and clinical surgeries thereof were approved in 1990's in Canada, Germany, Japan, etc. The photodynamic therapy is being world-widely used as therapy for esophageal cancer was approved in January 1996, and therapy for early lung cancer was approved in September in 1997 by the Food and Drug Administration (FDA).

However, the photodynamic therapy being currently utilized can not be used to voluminous tumor due to limitation of light transmittance, and causes side effects of photo-cytotoxicity since photosensitizer slowly reacts with a human body. Furthermore, since photosensitizer concentration inside tumor is low, therapeutic effectiveness is not enhanced. The photosensitizer may cause side effects by being accumulated in a human body for a long time, rather than serve as a photosensitizer for a therapy. Accordingly, required is a novel photosensitizer capable of reducing side effects by enhancing selection degree for tumor and capable of enhancing therapeutic effectiveness by laser irradiation.

Accordingly, the present inventors have developed a novel photosensitizer that has high selection and accumulation ratio for cancerous tissues, and reduces the conventional photo-cytotoxicity.

DISCLOSURE OF THE INVENTION

Therefore, it is an object of the present invention to provide a novel photosensitizer based on biocompatible polymer derivatives-photosensitizer conjugates for photodynamic therapy capable of remarkably increasing selection degree and accumulation ratio for cancerous tissues, remarkably reducing photo-cytotoxicity, and producing singlet oxygen or free radical by laser irradiation.

To achieve these objects, there is provided a novel photosensitizer based on biocompatible polymer derivatives-photosensitizer conjugates for photodynamic therapy capable of being selectively accumulated in cancerous tissues, and producing singlet oxygen or free radical by laser irradiation.

The biocompatible polymer derivatives include dextran, chitosan, glycol chitosan, poly-L-lysine, or poly-aspartic acid. As synthesized polymers, poly(N-2-(hydroxypropyl) methacrylamide), poly(divinyl ether-co-maleic anhydride), poly(styrene-co-maleic anhydride), or poly(ethylene glycol) may be used.

As the photosensitizer, phophyrins, chlorins, bacteriochlorins, or porphycenes may be used, and preferably, materials having a functional group such as carboxylic acid, amine, isothiocyanate may be used. More preferably, as the photosensitizer, protoporphyrin IX, bonellin, benzoporphyrin, or mono-aspartyl chlorine 6 may be used.

The photosensitizer based on biocompatible polymer derivatives-photosensitizer conjugates has a size corresponding to 100~300 nm in aqueous system.

To achieve these objects, there is also provided a photodynamic therapy using the photosensitizer based on biocompatible polymer derivatives-photosensitizer conjugates.

MODES FOR CARRYING OUT THE PREFERRED EMBODIMENTS

Figure 1:
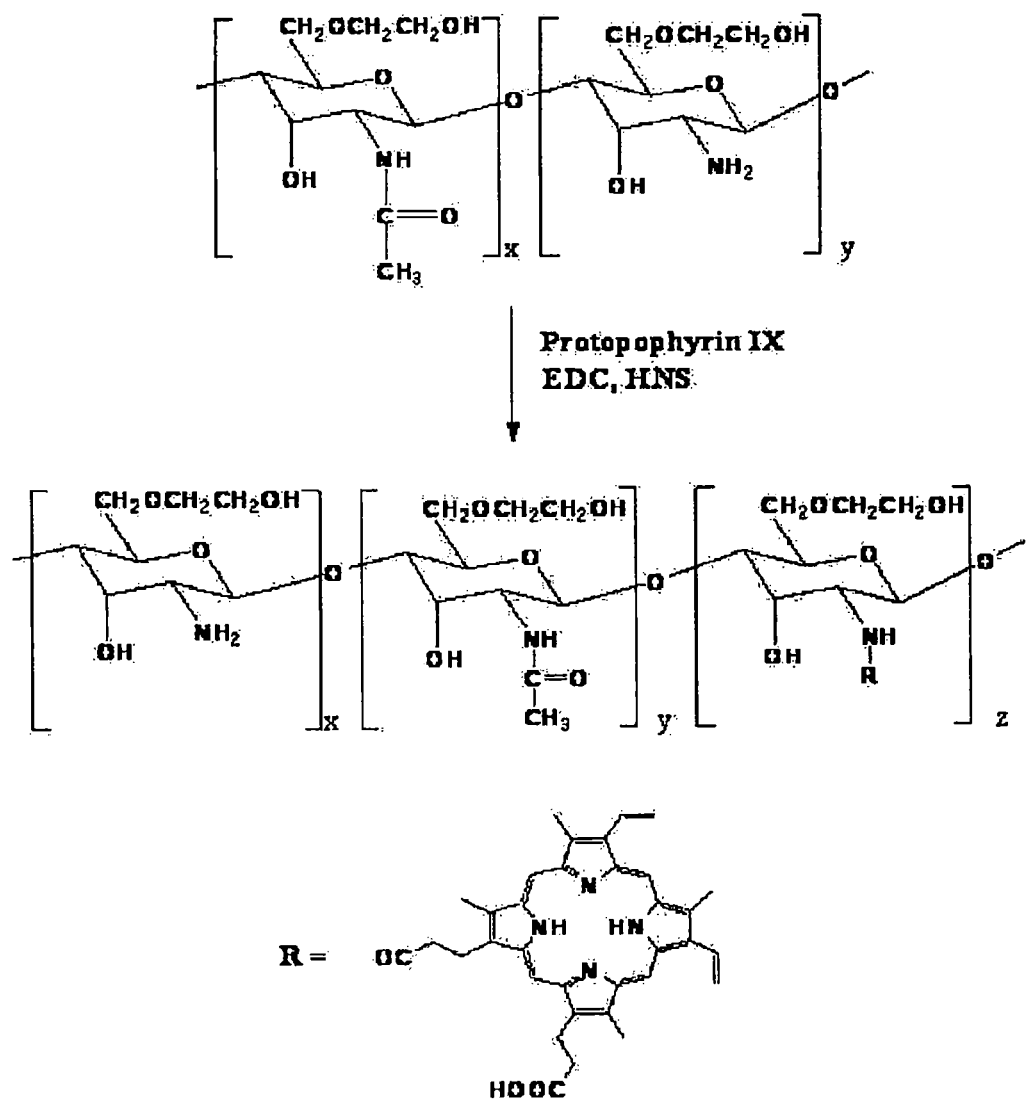
FIG. 1 is a chemical structure of novel chitosan polymer derivatives-photosensitizer conjugates for photodynamic therapy according to the present invention.

Reference will now be made in detail to the preferred embodiments of the present invention, examples of which are illustrated in the accompanying drawings.

Hereinafter, the present invention will be explained in more detail.

The present invention relates to a photosensitizer based on biocompatible polymer derivatives-photosensitizer conjugates for photodynamic therapy capable of being selectively accumulated in cancerous tissues and producing singlet oxygen or free radical by laser irradiation.

The conjugates are obtained by chemically reforming photosensitizer into biocompatible polymer derivatives, and stably form nano-sized self-assembly or self-aggregate in aqueous system through balance between hydrophile polymer derivatives and hydrophobic photosensitizer. The nano-sized biocompatible polymer derivatives have high selection and accumulation ratio for cancerous tissues, and is selectively accumulated around cancerous tissues due to EPR (Enhanced Permeability and Retention) resulting from high permeability of newl loose blood vessel around cancerous tissues. Furthermore, the photosensitizer may react with oxygen inside a human body by a specific laser wavelength, thereby producing singlet oxygen or free radical.

The polymer has to be provided with excellent biocompatibility and biodegradability within a living body, excellent stability within a living body to have high biodistribution within blood, and excellent accumulation ratio in cancerous tissues.

As the polymer derivatives, all types of polymers having biocompatibility within a living body may be used. Preferably, the polymer derivatives have to be provided with excellent biocompatibility and biodegradability within a living body, excellent stability within a living body to have high biodistribution within blood, and excellent accumulation ratio in cancerous tissues. The polymer derivatives may include materials having high accumulation ratio for cancerous tissues and capable of being used as drug delivery agents of anti-cancer preparations, such as dextran, chitosan, glycol chitosan, poly-L-lysine, or poly-aspartic acid. As synthesized polymers, poly(N-2-(hydroxypropyl)methacrylamide), poly(divinyl ether-co-maleic anhydride), poly(styrene-co-maleic anhydride), or poly(ethylene glycol) may be used.

Among the polymers, glycol chitosan having a large amount of positrons in high molecular chains has very high accumulation ratio for cancerous tissues at the time of preparing nano-sized particles. And, an amine group of the glycol chitosan serves to facilitate a chemical reforming of the photosensitizer.

As the photosensitizer of the present invention, phophyrins, chlorins, bacteriochlorins, or porphycenes may be used. Preferably, materials having a functional group such as carboxylic acid, amine, isothiocyanate may be used.

The polymer derivatives-photosensitizer conjugates of the present invention are stably formed as nano-sized particles in aqueous system, and are selectively accumulated in cancerous tissues according to characteristics of polymer nano-sized particles. Therefore, a problem of the conventional photosensitizer having a low molecular amount, toxicity to a human body is minimized. And, cells of cancerous tissues are induced to be eradicated by singlet oxygen or free radical produced by a specific laser wavelength. Accordingly, photodynamic therapeutic effectiveness may be maximized.

As an example of the polymer derivatives photosensitizer conjugates of the present invention, amphiphilic chitosan derivatives may be prepared by introducing hydrophobic photosensitizer to hydrophile glycol chitosan, chitosan polymer. The amphiphilic chitosan derivatives may be expressed as the following chemical formula 1.

[Chemical Formula 1]

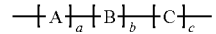

Here, the 'A' and 'B' are composed of N-acetylglucosamine and N-glucosamine derivatives, a repeating structure of glycol chitosan polymers. And, the 'C' is a photosensitizer, derivatives chemically coupled to glycol chitosan. The 'a' and 'b' have values of several hundreds~several ten thousands according to a molecular amount of glycol chitosan. And, the 'c' is a photosensitizer, and has a value of 20~100 in order to prepare nano-sized particles.

The polymer photosensitizer conjugates are prepared as self assembly type self-aggregated nano-sized particles, and have a size of 50~800 nm. The prepared polymer of nano-sized particles have excellent biocompatibility and accumulation ratio in cancerous tissues, and may produce singlet oxygen and free radical by a specific laser wavelength. Therefore, a laser wavelength becomes different according to a used photosensitizer, and the following table 1 shows activation wavelengths of various photosensitizers.

TABLE 1

| Activation wavelength of various photosensitizers | |
|---|---|
| Photosensitizers | Activation wavelengths |
| HPD porfimer sodium | 630 nm |
| BPD-MA | 689 nm |
| m-THPC | 652 nm |
| 5-ALA | 635 nm |
| 5-ALA-methylesther | 635 nm |
| 5-ALA benzylesther | 635 nm |
| 5-ALA hexylesther | 345-400 nm |
| SnET2 | 664 nm |
| Protoporphyrin IX | 635 nm |
| HPPH | 665 nm |
| Lutetium Texaphyrin | 732 nm |
| Phthalocyanine-4 | 670 nm |
| Taporfin sodium | 664 nm |

As a photosensitizer of the 'C', phophyrins, chlorins, bacteriochlorins, or porphycenes may be used, and preferably, protoporphyrin IX, bonellin, benzoporphyrin, or mono-aspartyl chlorine 6 (the following chemical formula 2) may be used. These materials may be chemically reformed.

[Chemical Formula 2]

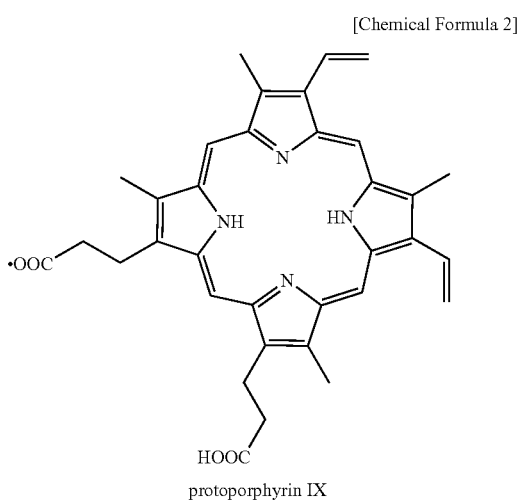

protoporphyrin IX

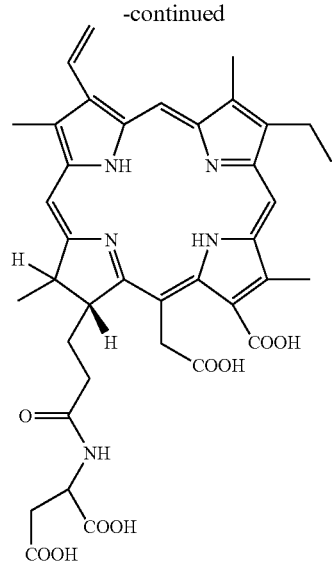

mono-aspartyl chlorin e6

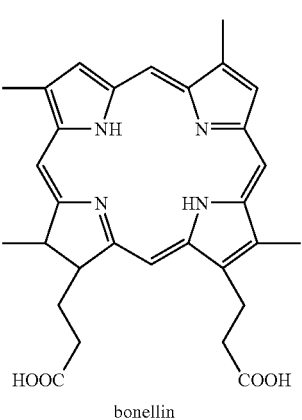

bonellin

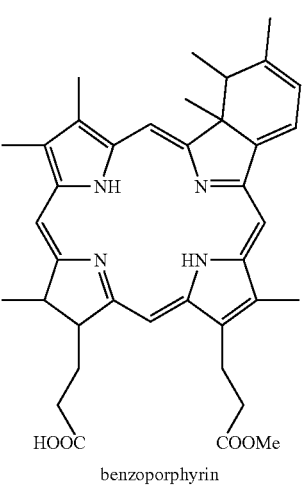

benzoporphyrin

When the biocompatible polymer derivatives-photosensitizer conjugates of nano-sized particles of the present invention are used, a selection degree and an accumulation ratio for cancerous tissues are remarkably increased thus to minimize photo-cytotoxicity of a photosensitizer inside a human body. Furthermore, when a specific laser wavelength is irradiated to conjugates accumulated into cancerous tissues with high selection degree and accumulation ratio, the conjugates react with oxygen inside a human body thus to produce singlet oxygen or free radical. The produced singlet oxygen or free radical induces cells of cancerous tissues to be eradicated. Therefore, when the polymer derivatives photosensitizer conjugates of the present invention are used for photodynamic therapy, side effects as a photosensitizer are reduced whereas photodynamic therapeutic effectiveness increases.

Hereinafter, the present invention will be explained in more detail with reference to the following preferred embodiment and experimental examples. It should be noted that the following preferred embodiment and experiment examples serve as examples of the present invention, and thus claims of the present invention are not limited thereto.

EXAMPLE 1

Preparation for Chitosan-PpIX Conjugates 100 mg of glycol chitosan was dissolved in 60 ml of water, and 20 ml of methanol was added to the results. Then, 50 mg of protoporphyrin IX (PpIX) expressed as a chemical formula I was dissolved in 50 ml of methanol, and then is slowly dropped into glycol chitosan solution. Then, 1-ethyl-3-(3-dimethyl-aminopropyl) carbodiimide (EDC) and N-hydrosuccinimide (NHS) corresponding to 1.5 mole of the PpIX were added to the results, and a stirring process was performed for 24 hours at a room temperature. Then, the reaction solution was dialyzed for two days to remove non-reacted PpIX and then to be freeze-dried, thereby preparing PpIX-chitosan conjugates. This reaction is expressed as the following reaction equation 1.

[Reaction Equation 1]

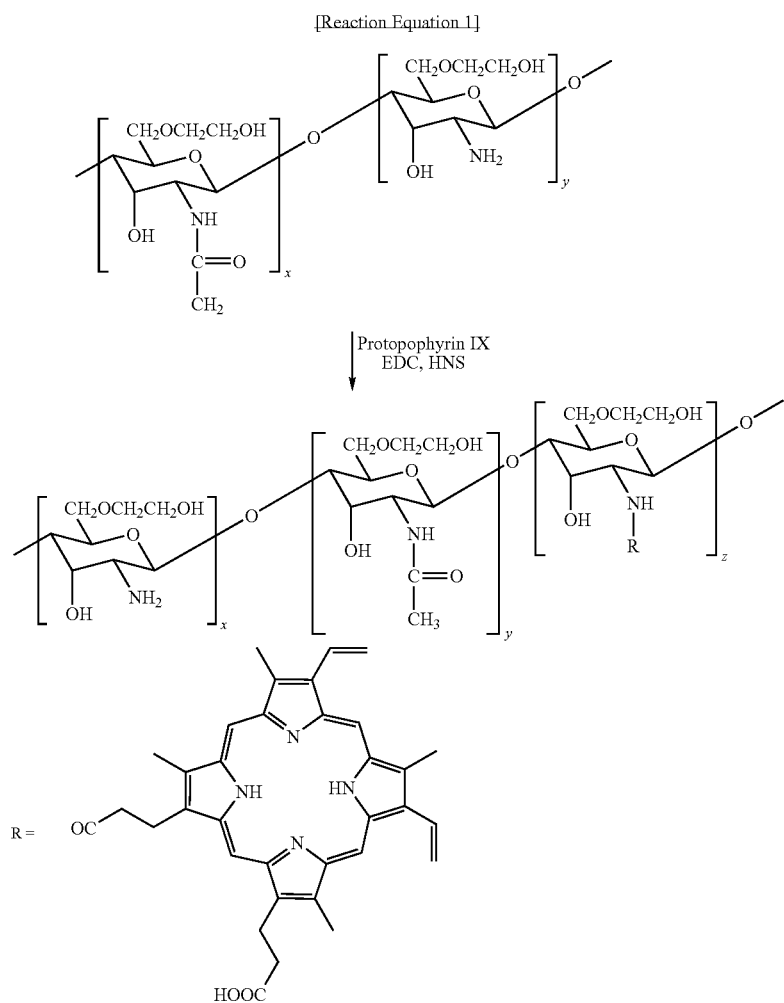

EXPERIMENTAL EXAMPLE 1

Analysis for Characteristics of Chitosan-PpIX Conjugates 1 mg of the chitosan-PpIX conjugates prepared in Example 1 was dissolved in 1 ml of DMSO, and light absorbing degree thereof was measured at a wavelength of 406 nm, thereby measuring an amount of the PpIX coupled to the chitosan. Here, the amount of the PpIX coupled to the chitosan was calculated from a black curved line. It was observed that about 16% of the PpIX by weight was coupled to the chitosan.

The chitosan-PpIX conjugates prepared in the preferred embodiment 1 were spread to 1 ml of PBS solution, thereby being sonicated for one minute at 80 W. Then, the chitosan-PpIX was filtered by a filter having 0.45 μm, so that a size and a shape of the particles were analyzed by a dynamic light scattering (DLS) and transmission electron microscopes (TEM).

Figure 2:
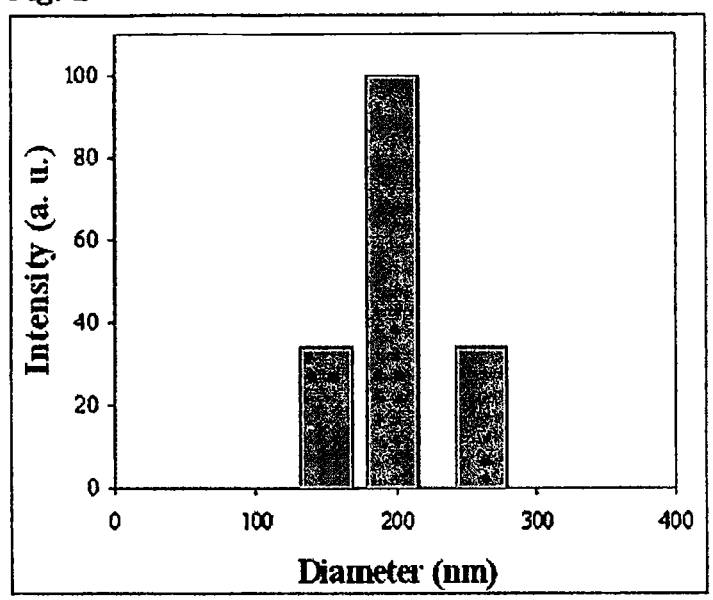
FIG. 2 shows a measured result about size distribution for nano-sized particles of chitosan PpIX conjugates prepared in a first preferred embodiment using a light scattering apparatus.
Figure 3:
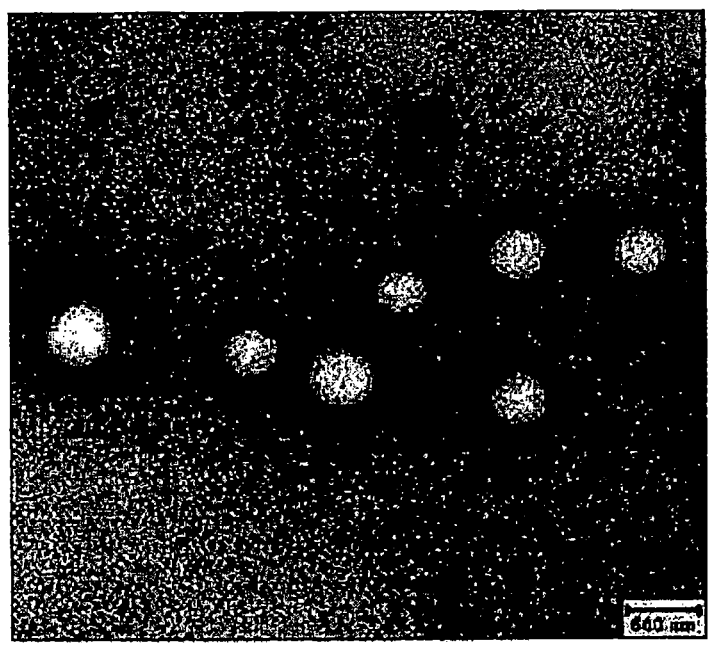
FIG. 3 is a photo of transmission electron microscopes (TEM) for the nano-sized particles of FIG. 2.

As shown in FIGS. 2 and 3, it was observed that the chitosan-PpIX conjugates have a diameter of 100~300 nm as a particle size. It was also observed by transmission electron microscopes (TEM) that the chitosan-PpIX conjugates have a diameter of 200~300 nm as an average particle size.

EXPERIMENTAL EXAMPLE 2

Test about Ability to Produce Singlet Oxygen by Chitosan-PpIX Conjugates

In order to use the chitosan-PpIX conjugates prepared in the Example 1 as a photosensitizer for photodynamic therapy, an ability to produce singlet oxygen by nano-sized particles of the chitosan-PpIX conjugates was compared with that of PpIX having a low molecular amount according to laser irradiation.

1 mg of chitosan-PpIX conjugates were dissolved in 10 ml of 0.1M $SDS/D_2O$ solvent, and then were diluted so that a final concentration can be 5 μg/ml. Then, light absorbing degree was measured at a wavelength of 400 nm by using a UV-vis spectrometer. Next, anthracene-9,10-dipropionic acid for detecting singlet oxygen was dissolved in $D_2O$ solution, thereby having a concentration of 5.5M. 20 μl of solution in which anthracene-9,10-dipropionic acid is dissolved was added to the chitosan-PpIX solution, and light absorbing degree of the results was measured at a wavelength of 400 nm. Laser was irradiated at 2-minute intervals by using He—Ne laser of 633 nm in which PpIX can produce singlet oxygen. Then, light absorbing degree of was measured at a wavelength of 400 nm. It was observed that a produced amount of singlet oxygen corresponded to a decreased light absorbing degree.

Figure 4:
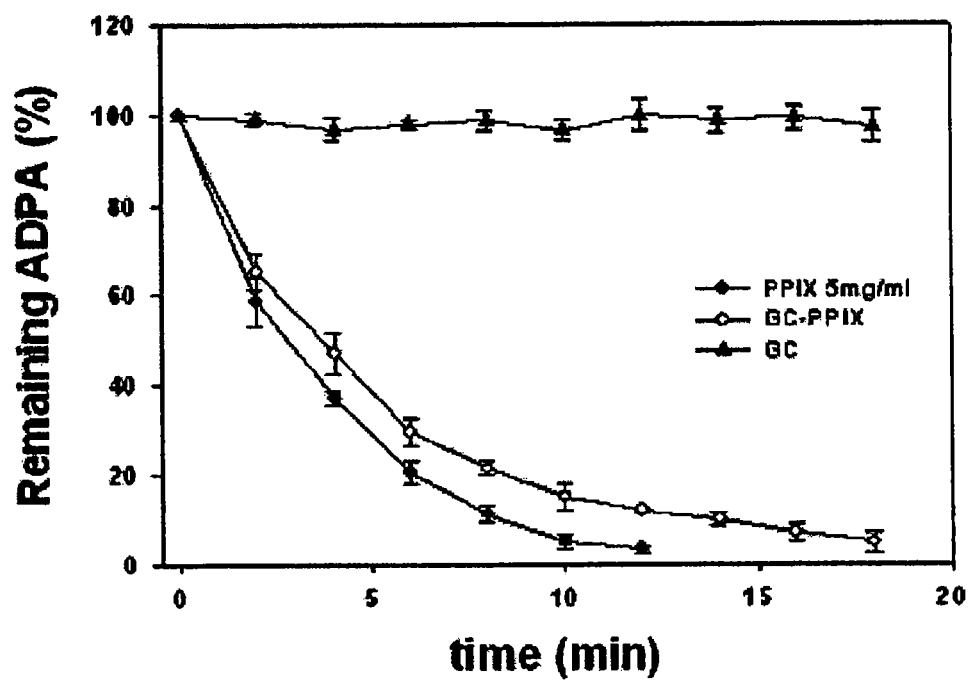
FIG. 4 is a graph showing an ability to produce singlet oxygen by the chitosan PpIX conjugates prepared in Example 1 by laser irradiation.

As shown in FIG. 4, it was observed that the chitosan-PpIX conjugates of nano-sized particles of the present invention can produce almost same amount of singlet oxygen as PpIX having a low molecular amount.

EXPERIMENTAL EXAMPLE 3

Test about Photo-Cytotoxicity of Chitosan-PpIX Conjugates

In order to use as a photosensitizer for photodynamic therapy, photo-cytotoxicity of the chitosan-PpIX conjugates prepared in Example 1 was tested. The photo-cytotoxicity test was performed by putting cultured cells (melanoma, B16F10, $1\times10^4$) in a 96 well plate for one day, and then by processing the cells with PpIX, chitosan, and chitosan-PpIX of different concentrations. Then, the chitosan-PpIX conjugates were washed with culture solution after 12 hours, and were cultured for 4 hours by processing MTT solution. Then, the chitosan-PpIX conjugates were dissolved in DMSO, and light absorbing degree of the results was measured at 570 nm.

Figure 5:
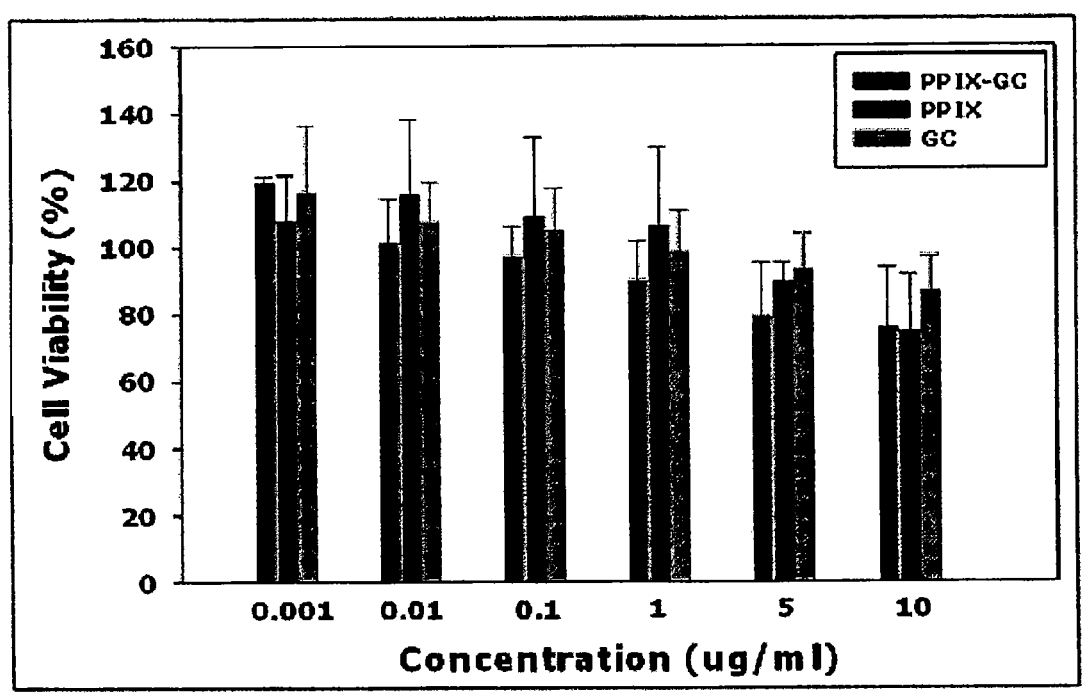
FIG. 5 is a graph showing photo-cytotoxicity for melanoma cells by the chitosan PpIX conjugates prepared in Example 1.

Referring to FIG. 5, the chitosan-PpIX conjugates showed no photo-cytotoxicity at a concentration less than 1 μg/ml, whereas the chitosan-PpIX conjugates showed photo-cytotoxicity at a concentration more than 1 μg/ml.

EXPERIMENTAL EXAMPLE 4

Test about Photo-Cytotoxicity of Chitosan-PpIX Conjugates through Laser Irradiation The chitosan-PpIX conjugates of the present invention corresponding to 5 μg/ml of PpIX were added to cultured cells (melanoma, B16F10, $1\times10^5$), and were cultured for 2 hours to be absorbed into the cells. Then, 633 nm laser was irradiated to the chitosan-PpIX conjugates, thereby testing photo-cytotoxicity. The photo-cytotoxicity test was performed by changing a total irradiation time of laser into 2, 6, and 12 minutes.

Figure 6:
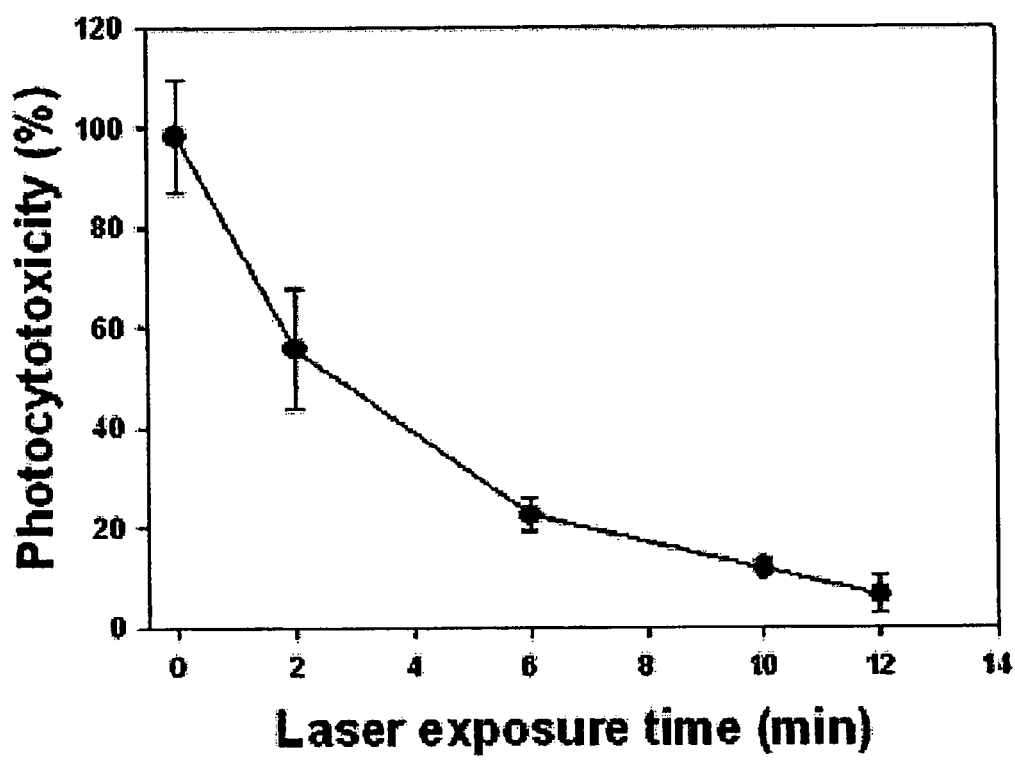
FIG. 6 is a graph showing a survival rate of cells absorbed into the chitosan PpIX conjugates prepared in Example 1 according to laser irradiation time.

Referring to FIG. 6 showing a cell survival rate according to laser irradiation time, a cell survival rate was remarkably reduced as laser irradiation time increased. Especially, when laser was irradiated for 12 minutes, 95% of cells were eradicated.

EXPERIMENTAL EXAMPLE 5

Observation for Eradication of Cancer Cells through Laser Irradiation to Chitosan-PpIX Conjugates The chitosan-PpIX conjugates of the present invention corresponding to 5 μg/ml of PpIX were added to cultured cells (melanoma, B16F10, $2\times10^5$), and was cultured for 2 hours thus to be absorbed into the cells. Then, 633 nm laser was irradiated to the chitosan-PpIX conjugates. It was observed that the cancer cells were eradicated. After laser irradiation for 12 minutes, the cancer cells were cultured for 12 hours. Then, it was observed that the cancer cells were eradicated through a TUNEL method.

Figure 7:
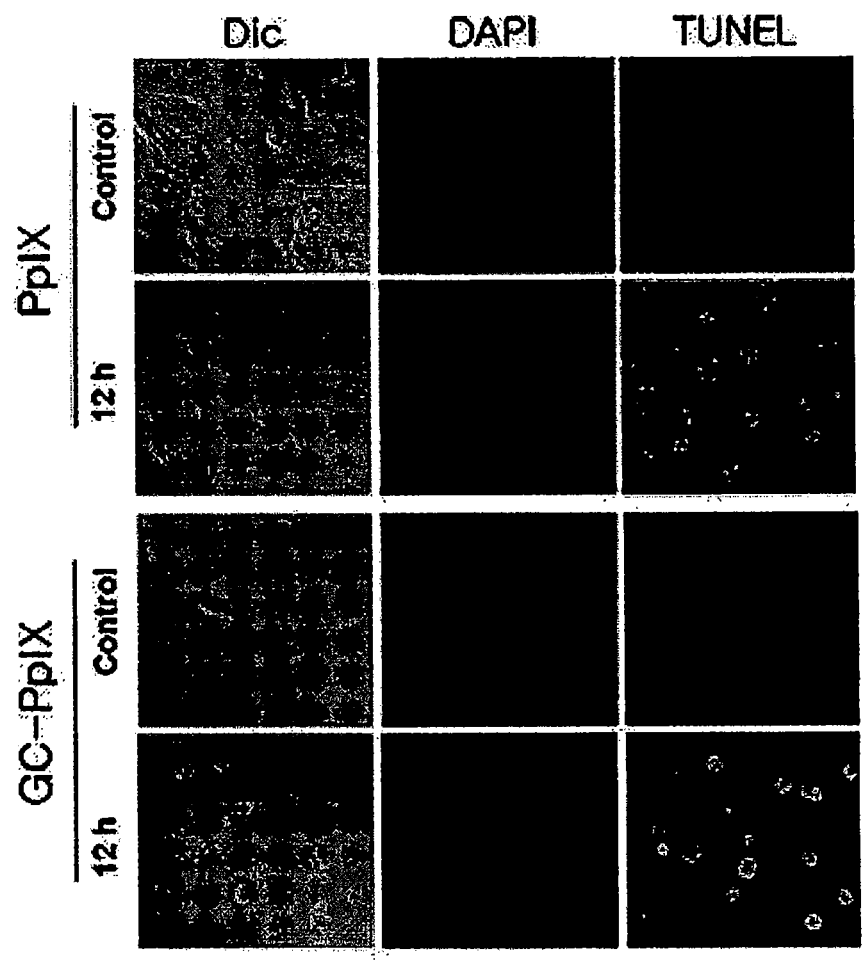
FIG. 7 is a graph showing a result of cancer cells absorbed into the chitosan PpIX conjugates prepared in Example 1, then irradiated by laser irradiation, then cultured for 12 hours, and then destroyed by a TUNEL dye method.

Referring to FIG. 7 showing that cancer cells having been irradiated with laser were cultured for 12 hours and then were eradicated through a TUNEL method, it was observed that cancer cells having been irradiated with laser were almost eradicated, while cancer cells having not been irradiated with laser survived.

EXPERIMENTAL EXAMPLE 6

Test about Chitosan-PpIX Conjugates Targeted to Cancerous Tissues

The chitosan-PpIX conjugates of the present invention corresponding to 30 mg/kg of PpIX by concentration were injected into tail veins of mice having SCC7 solid tumor of approximately 6-7 mm. Then, accumulation degree of the chitosan-PpIX conjugates to cancerous tissues was observed as phosphor intensity by using eXplore Optix according to time. As a control group, 30 mg/kg of PpIX was injected to the same mice having solid tumor, and at the same time, phosphor intensity in the cancerous tissues was observed.

Figure 8:
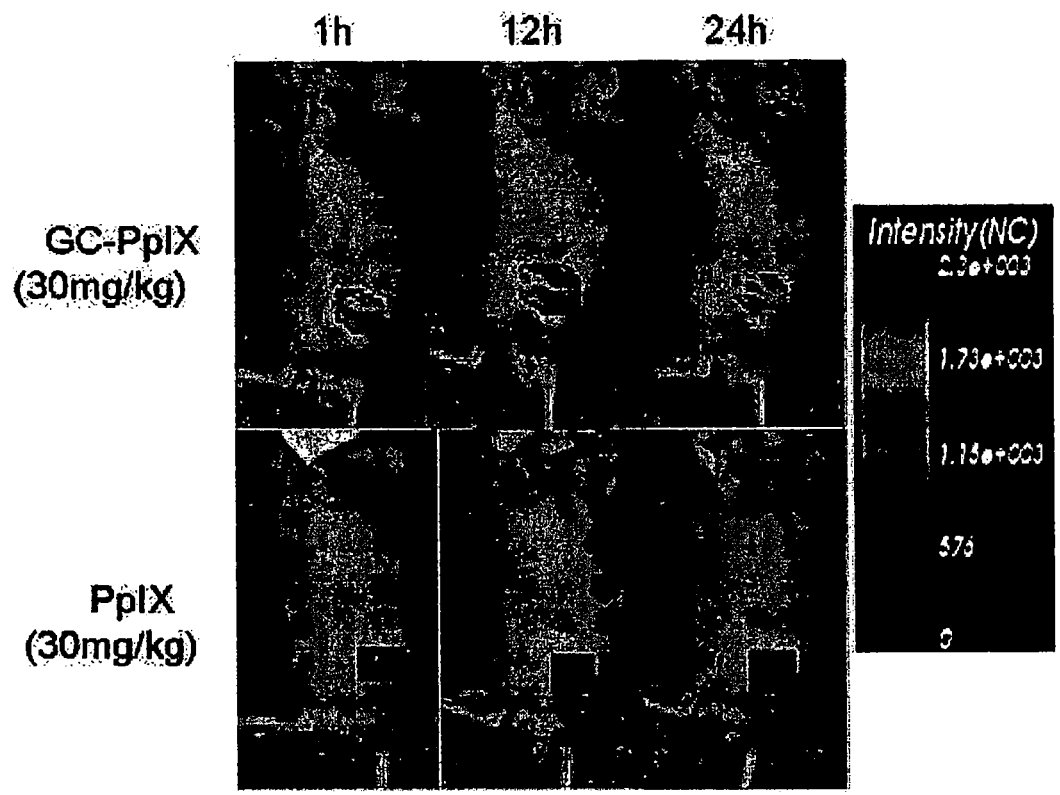
FIG. 8 shows a result that phosphor intensity increased in cancerous tissues according to time when the chitosan PpIX conjugates prepared in Example 1 was applied.

Referring to FIG. 8 showing that phosphor intensity of cancerous tissues increased according to time when chitosan-PpIX was injected into the cancerous tissues, it was observed that the chitosan-PpIX was accumulated to the cancerous tissues. When compared with PpIX, a much larger amount of chitosan-PpIX was injected to cancerous tissues. Therefore, it can be known that the chitosan-PpIX conjugates have higher photodynamic therapeutic effectiveness than the conventional photosensitizer.

EXPERIMENTAL EXAMPLE 7

Test about Photodynamic Therapeutic Effectiveness by Chitosan-PpIX Conjugates

The chitosan-PpIX conjugates of the present invention corresponding to 30 mg/kg of PpIX by concentration were injected into tail veins of mice having SCC7 solid tumor of approximately 6-7 mm. After 24 hours, 633 nm laser was injected to cancerous tissues for 12 minutes, and it was observed that cancer cells in the cancerous tissues were destroyed and eradicated. As a control group, 30 mg/kg of PpIX was injected to veins of mice. After 24 hours, laser was irradiated to the control group for 12 minutes to observe the control group.

Figure 9:
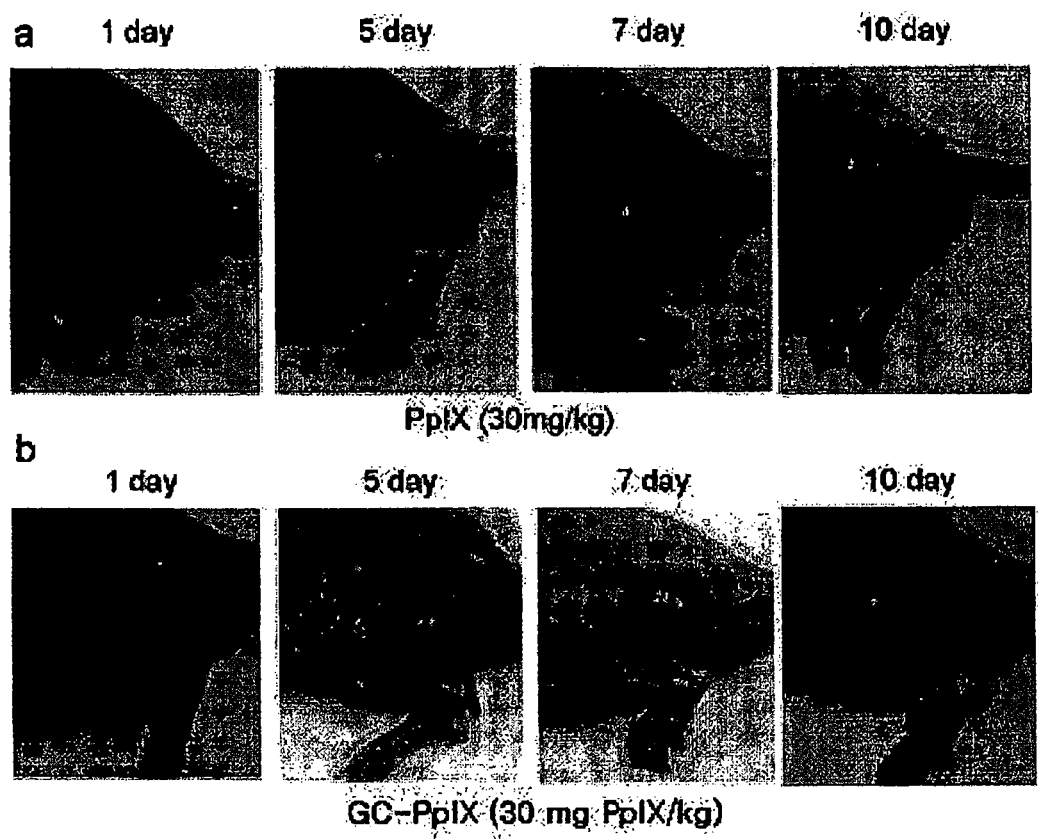
FIG. 9 is a photo showing a result that cancer cells were destroyed and necrotized in cancerous tissues when laser was irradiated into mice tails injected with chitosan PpIX conjugates.

Referring to FIG. 9, when laser was irradiated to mice tails injected with chitosan-PpIX, cancer cells in cancerous tissues were destroyed and eradicated. On the contrary, cancer cells in cancerous tissues injected with PpIX were scarcely destroyed and eradicated. Therefore, it was observed that nano-sized particles of the chitosan-PpIX conjugates according to the present invention were accumulated to cancer cells, thus to produce singlet oxygen by laser irradiation and thus to eradicate the cancer cells. Therefore, the chitosan-PpIX enhances photodynamic therapeutic effectiveness as an excellent photosensitizer.

The present invention has the following advantages.

As aforementioned, the photosensitizer based on biocompatible polymer derivatives-photosensitizer conjugates according to the present invention has excellent selection degree and accumulation ratio for cancerous tissues, and produces singlet oxygen or free radical by a specific laser wavelength. Furthermore, the photosensitizer based on biocompatible polymer derivatives-photosensitizer conjugates according to the present invention reduces side effects and implements enhanced therapeutic effectiveness by minimizing photo-cytotoxicity of the conventional photosensitizer having a low molecular amount.

It will also be apparent to those skilled in the art that various modifications and variations can be made in the present invention without departing from the spirit or scope of the invention. Thus, it is intended that the present invention cover modifications and variations of this invention provided they come within the scope of the appended claims and their equivalents.

The invention claimed is:

1. A photosensitizer based on biocompatible hydrophilic polymer derivatives-hydrophobic photosensitizer conjugates for photodynamic therapy,
    wherein the biocompatible polymer derivatives are chitosan, or glycol chitosan,
    wherein the photosensitizer comprises phophyrins, chlorins, bacteriochlorins, or porphycenes, and
    wherein the photosensitizer based on biocompatible hydrophilic polymer derivatives-hydrophobic photosensitizer conjugates for photodynamic therapy is selectively accumulated in cancerous tissues, is able to produce singlet oxygen or free radical by laser irradiation, and has a size of 100-300 nm in an aqueous system.

2. The photosensitizer based on biocompatible polymer derivatives-photo sensitizer conjugates for photodynamic therapy of claim 1, wherein the phophyrins, chlorins, bacteriochlorins, or porphycenes have a functional group such as carboxylic acid, amine, or isothiocyanate.

3. The photosensitizer based on biocompatible polymer derivatives-photosensitizer conjugates for photodynamic therapy of claim 2, wherein materials having the functional group such as carboxylic acid, amine, or isothiocyanate comprise protoporphyrin IX, bonellin, benzoporphyrin, or monoaspartyl chlorine 6.

* * * * *